Figure 1:
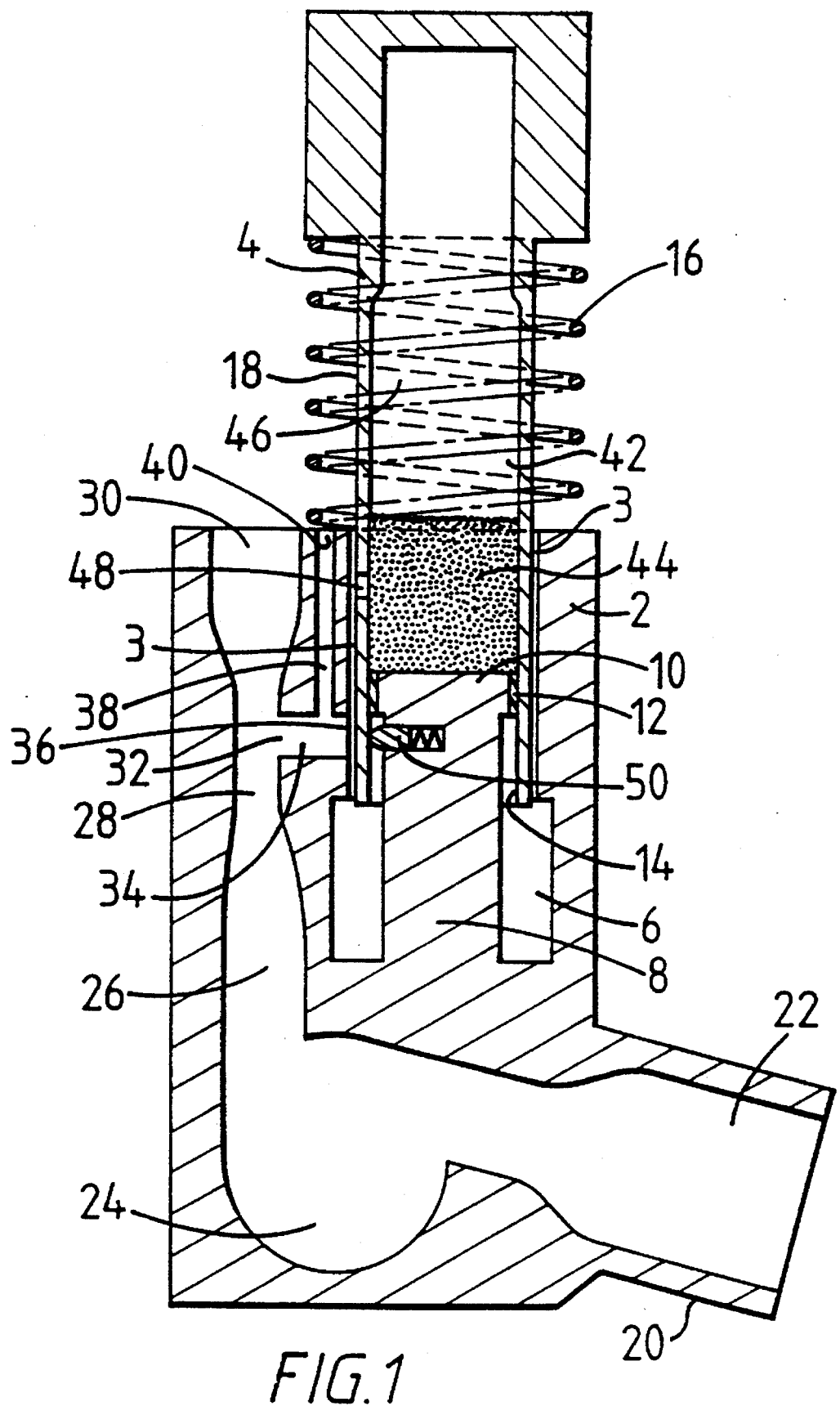

United States Patent [19]

Bacon

[11] Patent Number: 5,503,144

[45] Date of Patent: Apr. 2, 1996

[54] POWDERED MEDICAMENT DISPENSING DEVICE

[75] Inventor: Raymond Bacon, Portsmouth, United Kingdom

[73] Assignee: Norton Healthcare Limited, Harlow, United Kingdom

[21] Appl. No.: 39,304

[22] PCT Filed: Nov. 29, 1991

[86] PCT No.: PCT/GB91/02117

§ 371 Date: Apr. 22, 1993

§ 102(e) Date: Apr. 22, 1993

[87] PCT Pub. No.: WO92/10229

PCT Pub. Date: Jun. 25, 1992

[30] Foreign Application Priority Data

Dec. 15, 1990 [GB] United Kingdom ............... 9027234

[51] Int. Cl.$^6$ .................. A61M 15/08; A61M 16/00; B05D 7/14; B65D 83/06
[52] U.S. Cl. .................. 128/203.15; 128/203.19; 128/203.23; 128/203.28
[58] Field of Search .............. 128/200.14, 203.12, 128/203.15, 203.23, 203.19, 203.28

[56] References Cited

U.S. PATENT DOCUMENTS

| | | | |
|---|---|---|---|
| 4,344,573 | 8/1982 | De Felice | 128/203.15 |
| 4,446,862 | 5/1986 | Baum et al. | 128/203.15 |
| 4,570,630 | 2/1986 | Elliott et al. | 128/203.15 |
| 5,046,493 | 9/1991 | Kropkowki et al. | 128/203.15 |
| 5,113,855 | 5/1992 | Newhouse | 128/203.15 |
| 5,161,524 | 11/1992 | Evans | 128/203.15 |
| 5,201,308 | 4/1993 | Newhouse | 128/203.15 |
| 5,239,992 | 8/1993 | Bougamont et al. | 128/203.15 |
| 5,341,801 | 8/1994 | Zechner | 128/203.15 |

FOREIGN PATENT DOCUMENTS

| | | | |
|---|---|---|---|
| 288671 | 6/1953 | Switzerland | 128/200.22 |
| 9007351 | 7/1990 | WIPO | 128/203.15 |
| 9210228 | 6/1992 | WIPO | 128/203.15 |

*Primary Examiner*—Kimberly L. Asher
*Attorney, Agent, or Firm*—Nikaido, Marmelstein, Murray & Oram

[57] ABSTRACT

A powder inhalation device includes a powder reservoir which contains a powdered medicament and a volume of air. The volume of air is disposed between an upper surface of the powdered medicament and a cover member of the powder reservoir. A metering chamber extends from the powder reservoir, and an apparatus is included for compressing the volume of air within the reservoir. A passage extending from the reservoir to the atmosphere is provided to allow air to vent from the powder reservoir, through the metering chamber, and into the atmosphere as the pressure of the volume of air in the powder reservoir is increased by the compressing apparatus. The volume of air thereby causes the powdered medicament to be forced into the metering chamber, and through a selectively openable barrier into an inhaling chamber.

10 Claims, 3 Drawing Sheets

POWDERED MEDICAMENT DISPENSING DEVICE

BACKGROUND OF THE INVENTION

1. Field of the Invention

This invention relates to a dispensing device which is suitable for the dispensing and administration of a metered amount of powder. Such a device would be suitable for the dispensing and administration of pure powder form drugs or drugs mixed with a suitable carrier agent, e.g. lactose.

Metered dose inhalers are well known and often comprise a pressurized aerosol dispensing container. The aerosols contain gas propellants in which the powdered medicament is suspended. Upon actuation, the aerosol contents are expelled, through a metering valve, and a metered dose is propelled into the lungs of the patient.

Research has indicated that some aerosol propellants, including those used in metered does inhalers, can cause depletion of the ozone layer in the atmosphere. It has thus become more important that such inhalers can be substituted with metered dose inhalers which do not have a damaging effect on the environment. Furthermore, such aerosol systems are not suitable for some patients.

2. Description of the Prior Art

Several types of powder inhalers are known. Usually a metered dose of medicament is initially contained in a container. The container is often in the form of a gelatin capsule. The capsule is first opened, such as by piercing with a pin, and then its contents are dispersed and expelled by ensuring that airflow, due to the inhalation of the patient, causes the capsule to rotate.

These powder dispensers have several disadvantages. It is necessary for the patient to reload the dispenser after each dose release, and in some devices the capsules must be pierced before loading. Complicated mechanisms are employed to ensure complete expulsion of powder in order to provide the correct dose to the patient. This can make the devices difficult to operate and expensive to manufacture.

GB 2102295 and GB 2144997 disclose a complicated inhaler in which a metered dose of medicament is dispensed from a storage chamber containing powdered medicament in a pelletized micronized form. The inhaler includes a dosing unit which is connected to a storage chamber for the medicament. The dosing unit comprises a perforated rotating membrane, and spring loaded scrapers to fill the rotating perforations with medicament. The filled perforations are introduced to a passage which connects a propellant container to a nozzle. An amount of propellant is released when the patient depresses two triggers in succession. The propellant expels the contents of the exposed perforations towards the nozzle to be inhaled by the patient. The size of the metered dose is determined by the size of the perforations and the number of perforations that are brought into the propellant passage.

Such a device is expensive to manufacture, and the dosage accuracy relies on the efficiency of the scrapers to fill the perforations. The perforations often need to be presented several times to the powdered medicament to ensure complete filling. For optimum effect the device also requires the patient to coordinate inhalation with the operation of propellant release. Many patients find this coordination difficult to achieve.

EP 0069715 discloses a device which attempts to overcome some of the aforementioned problems. There is disclosed a powder inhaler which is actuated by the airflow generated by the inhalation of the patient. A breath actuated device eliminates the problem of the coordination of manual actuation and inhalation. A propellant is no longer necessary to effect actuation. The device also uses a perforated membrane and spring loaded scrapers to provide a metered dose of medicament. The patient rotates a maneuvering unit by a certain amount. This rotates the perforated membrane with respect to the scrapers filling the perforations and exposing a certain number of them to an air passage. The air flow generated on inhalation passes through the perforations and the metered dose is inhaled by the patient. A rotating means is provided to disrupt the airflow so as to break up any aggregate particles which have been formed in the dosing unit.

This device has the disadvantage that the airflow generated on inhalation passes directly through the perforations which are then returned to the dry storage chamber for refilling. Any powder which has become lodged in the perforations may become contaminated by the air, and this is then mixed with the pure dry powder held in the chamber. If the perforations become partially blocked then a full dose of medicament will not be inhaled by the patient.

SUMMARY OF THE INVENTION

It is the object of this invention to provide a metered dose powder inhaler, wherein the powdered medicament is stored in a powder reservoir housed in the device. It is further object of the invention to provide such an inhaler which is simple in design yet overcomes the disadvantages experienced with prior art dispensers.

In one aspect of the invention there is provided a powder inhalation device comprising a powder reservoir capable of containing a powdered medicament and a volume of air, a metering chamber extending from the powder reservoir to allow removal of the powdered medicament from the reservoir in discrete amounts and a means for compressing the air in the reservoir wherein a passage is provided to allow air to vent from the powder reservoir, through the metering chamber and into atmosphere as the pressure of the air in the powder reservoir is increased.

In a preferred arrangement the reservoir may be housed in a thin walled cylinder-like structure which interconnects with the main body of the device. The cylindrical reservoir and the main body may interconnect by way of a bore located in the main body of the device. It is preferred that the walls of the cylinder are in close sliding contact with the bore, while allowing air to pass from the reservoir, through the metering chamber and into the atmosphere.

In a further arrangement, the metering chamber may be housed in the wall of the cylindrical reservoir. The chamber may comprise a hole in the wall of the powder reservoir. The hole is of a predetermined size to allow the desired dosage of powder to pass from the reservoir ready to be delivered to the main air conduit which enables the powdered medicament to be inhaled by a patient. The chamber may be sealed with a fine filter, or may be a depression in the wall with appropriate venting or leakage path provided. Certain hole shapes seem to provide better metering repeatability, as do different patterns of air leakage paths. Cylindrical chambers with their depth equal to the cylinder diameter are preferred.

It is preferred that the metering chamber is filled from the reservoir by the instigation of relative motion between the metering chamber and the powder bulk so that the air pressure on the powder bulk is increased, forcing the powder into the metering chamber whilst allowing air to pass in a small amount through the metering chamber and vent to atmosphere. While in the device according to the present invention it is preferred that the powder front should pass across the entrance to the metering chamber by relative motion of the powder and the metering chamber, it has been found that the metering chamber will be filled even if the powder bulk is in contact with the entrance to the chamber and the air pressure above the powder bulk increased.

The relative motion may be provided by depression of the cylinder into a bore in the main body of the device, while the bulk of the powder is kept stationary by a protrusion positioned inside the bore. The cylinder may be depressed by the operation of a lever capable of acting on the cylinder to keep it depressed. It is preferred that the protrusion is provided with a seal, such that the inner bore of the cylinder and the protrusion seal are in sliding airtight contact.

The pressure entered on the powder bulk may be increased by compressing a volume of air contained above the powder. It will be realized that although reference herein has been made to air, any gas may be included within the reservoir which does not react with the powder, such as nitrogen.

Although not wishing to be bound by theory, it is likely that a local fluidizing effect of the powder bulk may take place which aids metering, with the air flow through the chamber carrying powder into the chamber.

It will also be realized that since the metering effect seems to be caused primarily by air flow from the high pressure region within the air reservoir (and possibly powder) to a lower pressure region beyond the metering chamber, a similar effect could be created by producing a low pressure region outside the reservoir and metering chamber, and providing a pressure differential between the reservoir and this low pressure region to allow air flow. This is to be understood and included within the scope of the invention as claimed.

In a preferred arrangement, the metering chamber, once filled, is closed to separate the metered dose from the reservoir by causing the chamber to move past the protrusion located in the bore. The metered dose may be prevented from leaking into the bore in the main body by ensuring the cylinder walls and the bore are in close sliding contact, but spaced sufficiently to allow an air passage. The size of the air passage is linked to the powder particle size and should be sufficiently narrow that powder within the metering chamber will not escape. Many powdered drugs borne on carriers have an average particle diameter size of between 20 and 50 μm. Accordingly, the width of the air passageway is preferably from 10 to 100 μm, preferably 10 to 50 μm. The passageway can be achieved by utilizing surface imperfections.

An exit port may be provided in the bore which, when aligned with the metering chamber, allows the chamber to be emptied. Once the powder has been metered it must then be ejected from the metering chamber. While more accurate volumetric metering is achieved with a higher packing density in the metering chamber, ejection of a more tightly packed powder is clearly more difficult. The first part of this process requires isolation of the metering chamber from the bulk powder reservoir. This may be achieved by causing the reservoir volume to be moved away from the metering chamber until a sliding seal moves over (or over and past) the inner face of the metering chamber. In this embodiment the seal should be wide enough to prevent a leakage path occurring from the higher pressure reservoir via the metering chamber to a lower pressure area behind the sliding seal.

Ejecting may take the form of increased air flow through the metering chamber carrying out the metered powder, air flow past the chamber, e.g. by a venturi-like restriction, creating a negative pressure to suck out the powder, or by mechanical ejection. Any air flow techniques could use the patient inspired air, but it is likely that dense packing and small metering chamber sizes may make this difficult particularly in terms of resistance to air flow. However, there is good potential during actuation in the specifically described form of the device to produce a small volume of air, at a pressure considerably greater or lower than atmospheric, ('high energy air') which can be utilized for dose ejection, and possibly dispersion.

A further advantage of this technique is that inspired air does not come into direct contact with the metering chamber and surrounding walls. This could help prevent any risk of moisture contamination to the bulk powder from the inspired air contaminating the metering chamber and could be arranged to help avoid any such contamination risks should the patient breath out through the device.

Mechanical ejection techniques may preferably be combined with air flow techniques in order to remove powder which remains attached to the end of the ejector.

The metering chamber may also be in the form of a cup on a rotatable axis. Such a system is described in, for example, GB 2165159.

It is preferred that the air conduit allows air to enter an air inlet in the main body and flow to a mouthpiece, the air flow being caused by the inhalation of the patient. A venturi-type restriction and a secondary passageway may be included in the air conduit. The secondary passageway may connect the exit port to the restriction and further connect a secondary air inlet to the restriction. The air flow through the main inlet and secondary inlet transfers the metered dose to the patient for inhalation. Alternatively the air flow may be arranged to flow through the metering chamber.

The even distribution of the powder in the air flow before it is inhaled is preferably achieved by producing a turbulent air stream. This may be produced by including a swirl chamber in the air conduit.

It has been found that the most beneficial effect for patients is obtained when inspiration is carried out at at least 10 liters per minute, preferably at least 15 liters per minute. This may be achieved by incorporating a regulator within the inhalator to permit it to operate only at a minimal air flow of, e.g. 10 liters per minute.

BRIEF DESCRIPTION OF THE DRAWINGS

The present invention will be further described by way of example only, with reference to and illustrated in the accompanying drawings, wherein:

FIG. 1 is a sectional view according to an embodiment of the invention, in the rest position;

FIG. 2 is a sectional view according to an embodiment of the invention in the actuated position; and FIG. 3 is a sectional view of a further embodiment of the invention.

DETAILED DESCRIPTION OF THE PREFERRED EMBODIMENTS

As seen in FIGS. 1 and 2 an inhalation device consists of a main body 2 and thin-walled cylinder-like chamber 4.

The main body 2 includes a bore 6 coaxial with the cylinder 4 and a protrusion which forms a piston structure 8 inside the bore 6. The piston 8 is also coaxial with the cylinder 4.

The piston head 10 is provided with a circumferential seal 12. The seal 12 ensures that the piston 8 is in slidable airtight contact with the inner bore 14 of the cylinder 4.

A passageway 3 is provided by a selection of surface finish to allow controlled venting to the atmosphere.

The cylinder 4 is free to move longitudinally in the bore 6 but is prevented from rotational movement (not shown). A spring 16 is coiled coaxially around the cylinder 4. The cylinder walls 18 are in close sliding contact with the bore 6 separated by the air passageway 3. The spring 16 provides a means to bias the cylinder 4 in its rest position (shown in FIG. 1).

The main body 2 has a mouthpiece 20 connected by a passageway 22 to a swirl chamber 24. The swirl chamber 24 is in turn connected to a passage 26 which includes a venturi-type restriction 28 leading to an air inlet 30.

A side entry 32 in the narrow section of the restriction 28 leads to a secondary passage 34. The secondary passage 34 is connected to the main bore 6 by an exit port 36.

The main body 2 further includes a small bore 38. The small bore connects with the secondary passage 34 and is vented at a secondary air inlet 40 close to the air inlet 30.

The inner bore 14 of the cylinder 4, the piston head 10 and the piston seal 12 cooperate together to form a dry reservoir 42. The reservoir 42 contains a bulk of finely powdered medicament 44. A volume of air 46 is trapped above the medicament 44.

The cylinder wall 18 is provided with a metering chamber 48 comprising a hole in the cylinder wall 18. The volume of the metering chamber 48 is such that the amount of medicament which can be contained in that volume is equivalent to one dose.

Figure 2:
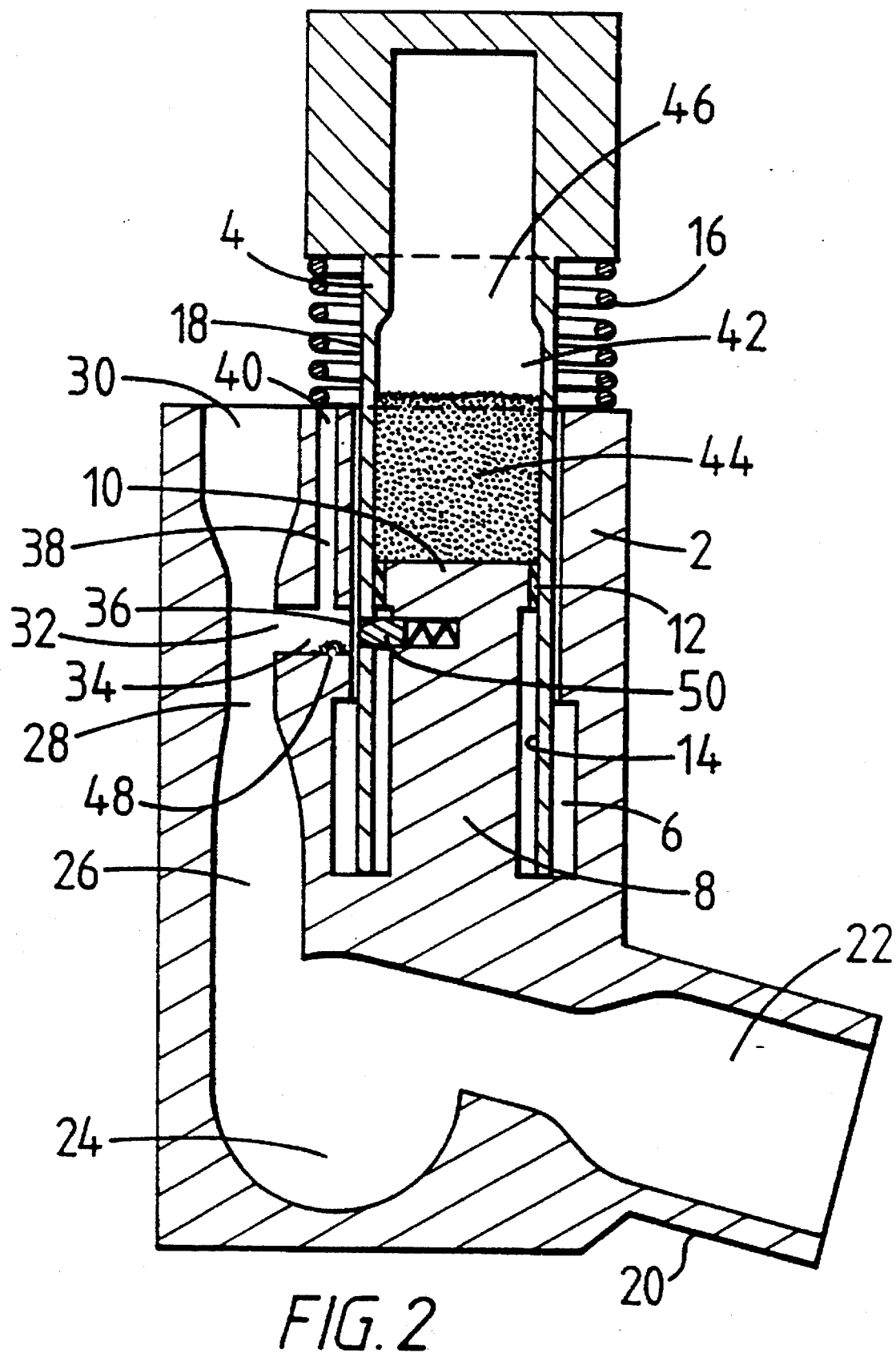
Figure 3:
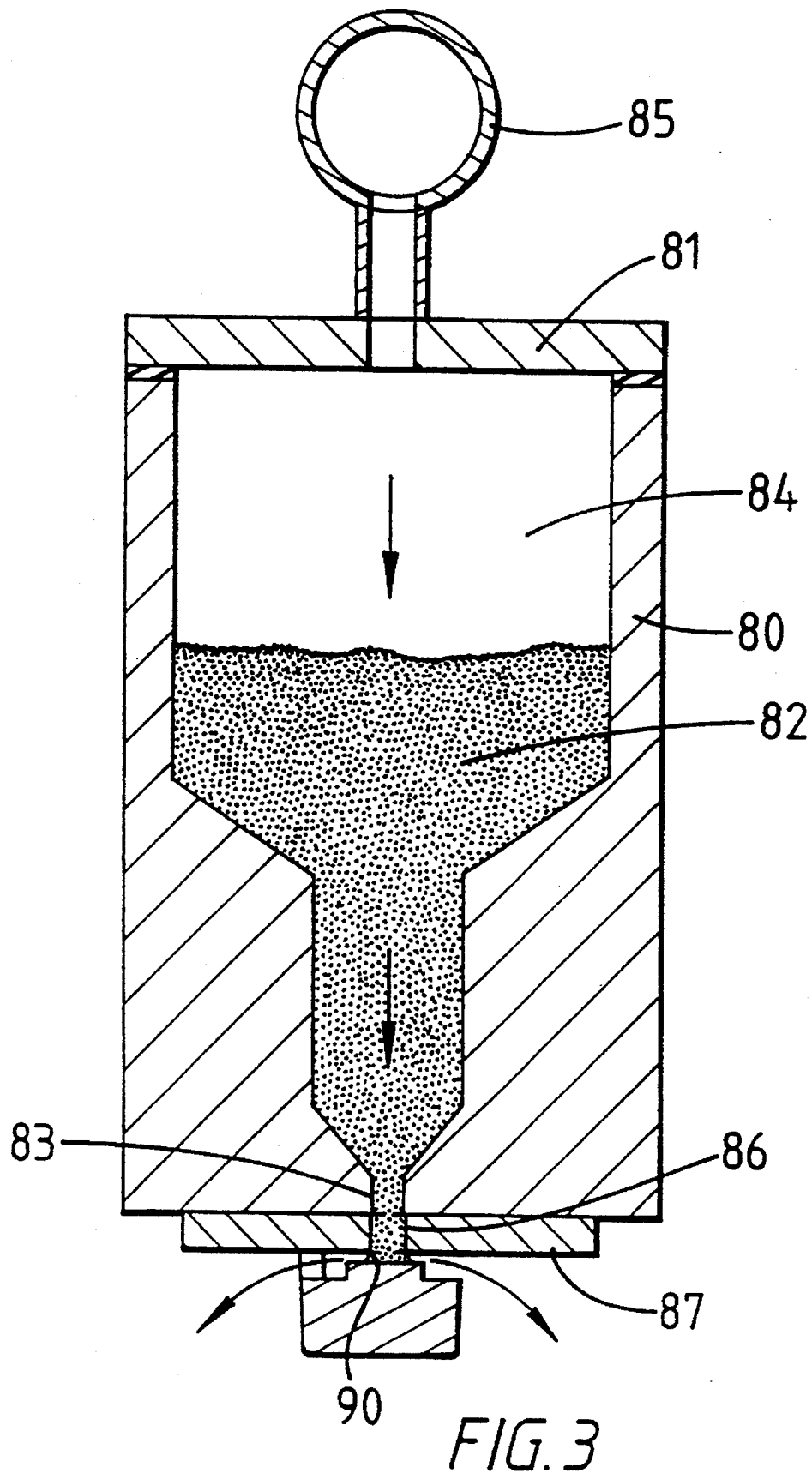

The metering chamber 48 is so positioned in the cylinder wall 18 that when the cylinder 4 is in its actuated position (as shown in FIG. 2) the metering chamber 48 is aligned with the exit port 36 in the main body 2.

The piston 8 is provided with a small spring loaded plunger 50. The plunger 50 is aligned with the centre line of the exit port 36. When the cylinder 4 is in the rest position (as shown in FIG. 1) the plunger is restrained from operation by the cylinder wall 18.

When the cylinder 4 is in the actuated position (shown in FIG. 2) the plunger is projected into the metering chamber 48.

The main body 2 of the dispensing device and the cylindrical structure 4 are preferably manufactured from a plastic such as polypropylene, acetal or moulded polystyrene. They may however be manufactured from metal or another suitable material.

The piston head seal 12 may be a seal of plastic such as PTFE, synthetic rubber or natural rubber. The seal 12 may be a cup or lip seal extending around the piston head 12.

In use, the patient holds the device such that the cylinder 4 is located uppermost. The patient then shakes the device, while holding it vertically. The shaking aids the mixing of the powdered medicament, and also ensures that the powder is deposited at the bottom of the cylinder 4 in contact with the piston head 10.

The patient then depresses the top of the cylinder 4. The spring 16 becomes compressed and the cylinder 4 moves down the bore 6 inside the main body 2.

As the cylinder 4 moves down the metering chamber 48 passes through the bulk of the medicament 44. At the same time, the air in the space 46 is compressed the volume enclosed by the cylinder walls 18 the piston head 10 and the piston seal 12 decreases. A small amount of air flows through the powder bulk 44, through the metering chamber 48, through the passageway 3 and into the atmosphere.

The combined action of the movement of the metering chamber 48 through the bulk medicament 44 the increase in pressure on the medicament and the air flow results in the filling of the chamber 48 with a metered dose of medicament.

The width of the passageway 3 is such that no medicament leaks out of the chamber 48.

The patient depresses the cylinder 4 until it reaches the end of its travel. The patient then inhales while keeping the cylinder 4 depressed.

In the actuated position (shown in FIG. 2) all the powdered medicament 44 except that in the metering chamber 48 is sealed in the volume defined by the cylinder walls 18, the piston head 10 and the piston seal 12.

When the cylinder 4 is fully depressed the metering chamber 48 is aligned with the exit port 36 in the main body 2 and the spring loaded plunger 50.

The plunger 50 is no longer restrained by the cylinder walls 18, and as it springs forward the powder in the metering chamber 48, is pushed into the passage 34 through the exit port 36. The plunger is restrained from further movement by suitable means (not shown).

The inhalation of the patient causes air to enter through the inlet 30. The air reaches the venturi-type restriction 28 and the narrowing of the inlet causes the air velocity to increase. The air pressure in the restriction 28 decreases as a result of the increase of velocity. The drop in pressure causes a further stream of air to enter through the small bore 38 which in turn causes the metered dose of medicament to be dragged into the main air stream flowing through the restriction 28.

The metered dose of medicament is carried in the air stream through the passage 26 into the swirl chamber 24.

The geometry of the swirl chamber 24 causes the air and the powder to flow a circular path. The turbulent air flow in the swirl chamber results in the dispersion of the powder in the air flow.

The particles are carried in the air stream through the passage 22 to the patient via the mouthpiece 20. The patient thus inhales air containing a metered dose of medicament.

After use, the patient releases the cylinder 4 and it returns to the rest position under the influence of the spring 68. The cylinder is provided with a limiting end stop (not shown) to prevent the cylinder and main body from becoming detached. As the cylinder 4 rises the plunger 50 is caused to retract by the movement of the cylinder wall 18 and the specific shape of the plunger 36. The enclosed space 46 returns to its original volume and the trapped air is no longer compressed.

The device is ready for further use.

The inhalation device may be manufactured as a sealed unit, which can be discarded when the level of the powdered medicament 44 falls below the level of the metering chamber 48. Alternatively, the reservoir may be refilled through an opening in the top of the cylinder 4 which is normally sealed by a plug.

In a further embodiment of the device, as seen in FIG. 3, an inhalation device includes a chamber 80 which will be within the main body of the device (not shown). A volume of powder 82 is included within the chamber 80. Above the powder 82 is a space 84 which is connected to a means 85 of increasing the pressure of the air within the space 84.

An orifice 83 leads from the chamber 80 into a metering chamber 86. This metering chamber 86 is formed in a plate 87 which is moveable relative to the body enclosing the chamber 80, in particular the orifice 83. Remote from the nozzle is an air gap 90.

As pressure is increased within the space 84, powder flows through the orifice 83 into the metering chamber 86. At the same time, air flows from the space 84 through the powder 82, through the orifice 83 and metering chamber 86 and out through the air gap 90 which is of such a size to prevent powder leakage. The metering chamber 86 is completely filled with powder.

The plate 87 is then slid sideways and the chamber 80 containing the metered dose of powder is presented to the dispersion system. In order to refill the chamber, an airtight removeable lid 81 is provided.

Suitable drugs which may be used with the include sabutamol, beclomethasone dipropionate, budesonide and sodium cromoglycate, and others.

I claim:

1. A powder inhalation device, comprising:

a powder reservoir, said powder reservoir containing a powdered medicament and a volume of air therein, said volume of air being enclosed above an upper surface of the powdered medicament;

a metering chamber extending from the powder reservoir;

a means for compressing the volume of air within the reservoir; and passage means extending from the reservoir to the atmosphere for venting air from the powder reservoir, through the metering chamber and into the atmosphere as the pressure of the volume of air in the powder reservoir is increased by the compressing means, the volume of air carrying powdered medicament into the metering chamber and through a selectively openable barrier into an inhaling chamber.

2. A powder inhalation device, comprising:

a powder reservoir, said powder reservoir containing a powdered medicament and a volume of air therein, said volume of air being disposed between an upper surface of the powdered medicament and a cover member of the powder reservoir;

a metering chamber extending from the powder reservoir;

a passage means for allowing air to vent from said powder reservoir through said metering chamber; and means for creating an air pressure difference between said powder reservoir and said passage means to cause an air flow from said powder reservoir through said metering chamber and into said passage means, the air flow carrying and forcing powdered medicament from the powder reservoir into the metering chamber and through a selectively openable barrier into an inhaling chamber.

3. An inhalation device according to claim 2 wherein the powder reservoir is partly defined by a thin-walled substantially cylindrical structure and the metering chamber is a hole defined in the wall of the powder reservoir.

4. An inhalation device according to claim 3 wherein the hole is in the form of a cylindrical chamber having a depth substantially equal to a diameter of the cylindrical chamber.

5. An inhalation device according to claim 2 wherein as the metering chamber is filled from the reservoir the bulk of the powder passes across the internal entrance to the metering chamber.

6. An inhalation device according to claim 5 wherein the means for creating air pressure difference is in sliding contact within a bore in the device, said bore having a protrusion positioned therewithin, the powder being held within the powder reservoir by the upper surface of the protrusion to form the powder reservoir.

7. An inhalation device according to claim 5 or claim 6 wherein the metering chamber, once filled with powder, is closed to separate the metered dose from the reservoir by causing the metering chamber to move past the upper surface of the protrusion located in the bore.

8. An inhalation device according to claim 2 wherein the air pressure difference is caused by air flow through a venturi-like restriction.

9. A powder inhalation device as recited in claim 2, wherein said metering chamber is disposed in a dose delivery structure, and is movable between a loading position wherein the metering chamber communicates with the powder reservoir, and a delivery position wherein the metering chamber communicates with a powder dispersion system.

10. A powder inhalation device as recited in claim 9, wherein said dose delivery structure comprises a slidably mounted plate member.

* * * * *